United States Patent
Otsubo et al.

(10) Patent No.: US 7,393,347 B2
(45) Date of Patent: Jul. 1, 2008

(54) DISPOSABLE PULL-ON TYPE WEARING ARTICLE

(75) Inventors: Toshifumi Otsubo, Kagawa-ken (JP); Naoto Ohashi, Kagawa-ken (JP); Yusuke Kawakami, Kagawa-ken (JP); Makoto Ichikawa, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/376,164

(22) Filed: Mar. 16, 2006

(65) Prior Publication Data

US 2006/0212019 A1 Sep. 21, 2006

(30) Foreign Application Priority Data

Mar. 17, 2005 (JP) ............................. 2005-077731

(51) Int. Cl.
*A61F 13/15* (2006.01)
*A61F 13/20* (2006.01)

(52) U.S. Cl. ................................. 604/385.01; 604/396

(58) Field of Classification Search ................. 604/380, 604/385.01, 385.03, 385.24, 396
See application file for complete search history.

(56) References Cited

U.S. PATENT DOCUMENTS 6,414,217 B1 * 7/2002 Uitenbroek et al. ......... 604/378

FOREIGN PATENT DOCUMENTS

| JP | 5-15551 | 1/1993 |
| JP | 2002-153509 | 5/2002 |
| WO | 97/13485 | 4/1997 |

* cited by examiner

*Primary Examiner*—Michele Kidwell
(74) *Attorney, Agent, or Firm*—Lowe Hauptman Ham & Berner LLP

(57) ABSTRACT

A disposable pull-on type wearing article has a front waist region and a rear waist region which are overlapped with each other along side edges thereof and integrated together at sealing spots so as to form lateral waist zones. A surface to come in contact with the wearer's skin in the respective lateral waist zones is provided with cover sheets each bonded to the front and rear waist regions so as to cross a border line between these front and rear waist region. Such an arrangement prevents the sealing spots from coming in contact with the wearer's skin.

19 Claims, 2 Drawing Sheets

DISPOSABLE PULL-ON TYPE WEARING ARTICLE

RELATED APPLICATIONS

The present application is based on, and claims priority from, Japanese Application Number 2005-77731, filed Mar. 17, 2005, the disclosure of which is hereby incorporated by reference herein in its entirety.

BACKGROUND OF THE INVENTION

The present invention relates to a disposable pull-on type wearing article including a disposable pull-on type diaper as an example.

Disposable pull-on type wearing articles used in the form of the pull-on type diaper or training pants are well known. According to a method and an apparatus for bonding components of a pull-on type wearing article disclosed in Japanese Unexamined Patent Application Publication No. 1993-15551, front and rear waist regions can be connected with each other using an ultrasonic sealing apparatus.

According to the invention disclosed in the above publication, when the top- and the backsheets together forming the front and rear waist regions of the wearing article contain a heat-sealable material such as thermoplastic synthetic fibers or a thermoplastic synthetic resin film, the front and rear waist regions may be put flat along opposite side edges of these regions and then treated by an ultrasonic sealing apparatus to connect these front and rear waist regions to each other. Specifically, the sealable material is molten and then solidified to form the sealing spots. However, the heat-sealable material such as the fibers or the film, even if it is intrinsically soft, is converted to a hard blocky structure in each of the sealing spots after molten and then solidified. When the wearing article having such sealing spots is put on the wearer's body with the front and rear waist regions tightened in a waist-surrounding direction, the sealing spots may uncomfortably irritate the wearer's skin from the inside of the wearing article.

SUMMARY OF THE INVENTION

In view of the problem as has been described above, it is an object of the present invention to provide a disposable pull-on type wearing article having front and rear waist regions sealed together along opposite side edges of these two regions at sealing spots improved so that the sealing spots do not irritate the wearer's skin from the inside of the wearing article.

According to the present invention, there is provided a disposable pull-on type wearing article comprising: a front waist region, a rear waist region, a crotch region, the front and rear waist regions respectively having side edges opposed to each other in a transverse direction of the article, the front and rear waist regions being overlapped with each other along the side edges and integrated together at sealing spots formed by a thermoplastic synthetic resin contained in these side edges to define a waist-opening, a pair of leg-openings and lateral waist zones opposed to each other in the transverse direction.

The disposable pull-on type wearing article further comprises cover sheets each bonded to the front and rear waist regions on a surface to come in contact with the wearer's skin in the respective lateral waist zones so as to cross a border line between these front and rear waist regions.

According to another preferred embodiment of the present invention, the cover sheets extend in the lateral waist zones between the waist-opening and the leg-openings.

According to still another preferred embodiment of the present invention, the cover sheets are bonded to the front and rear waist regions at least one of by means of adhesion and interlacing of component fibers contained in the front and rear waist regions and the cover sheets.

In the disposable pull-on type wearing article according to the present invention, the side edges of the front and rear waist regions are integrated at the sealing spots so as to form the lateral waist zones of the wearing article and the surface to come in contact with the wearer's skin in the respective lateral waist zones is provided with cover sheets. Such a unique arrangement prevents the sealing spots from coming in direct contact with the wearer's skin from the inside of the wearing article. There is therefore no possibility that the sealing spots might come in direct contact with the wearer's skin and irritate the skin even when this wearing article is put on the wearer's body and the front and rear waist regions are tightened in the waist-surrounding direction.

According to another preferred embodiment of the invention, the respective cover sheets extend between the waist-opening and the leg-openings. With such a unique arrangement, it is unlikely that the sealing spots in the respective lateral waist zones might come in contact with the wearer's skin in any point of the respective lateral waist zones.

According to still another preferred embodiment of the invention, the cover sheets may be bonded to the front and rear waist regions selectively by at least one of means of adhesion, sealing, and interlacing of the component fibers so that the selected means for bonding will result in no irritation of the wearer's skin.

DETAILED DESCRIPTION OF THE PREFERRED EMBODIMENTS

Details of a disposable pull-on type wearing article according to the present invention will be more fully understood from the description of a disposable pull-on type diaper as a typical embodiment of the invention given hereunder with reference to the accompanying drawings.

Figure 1:
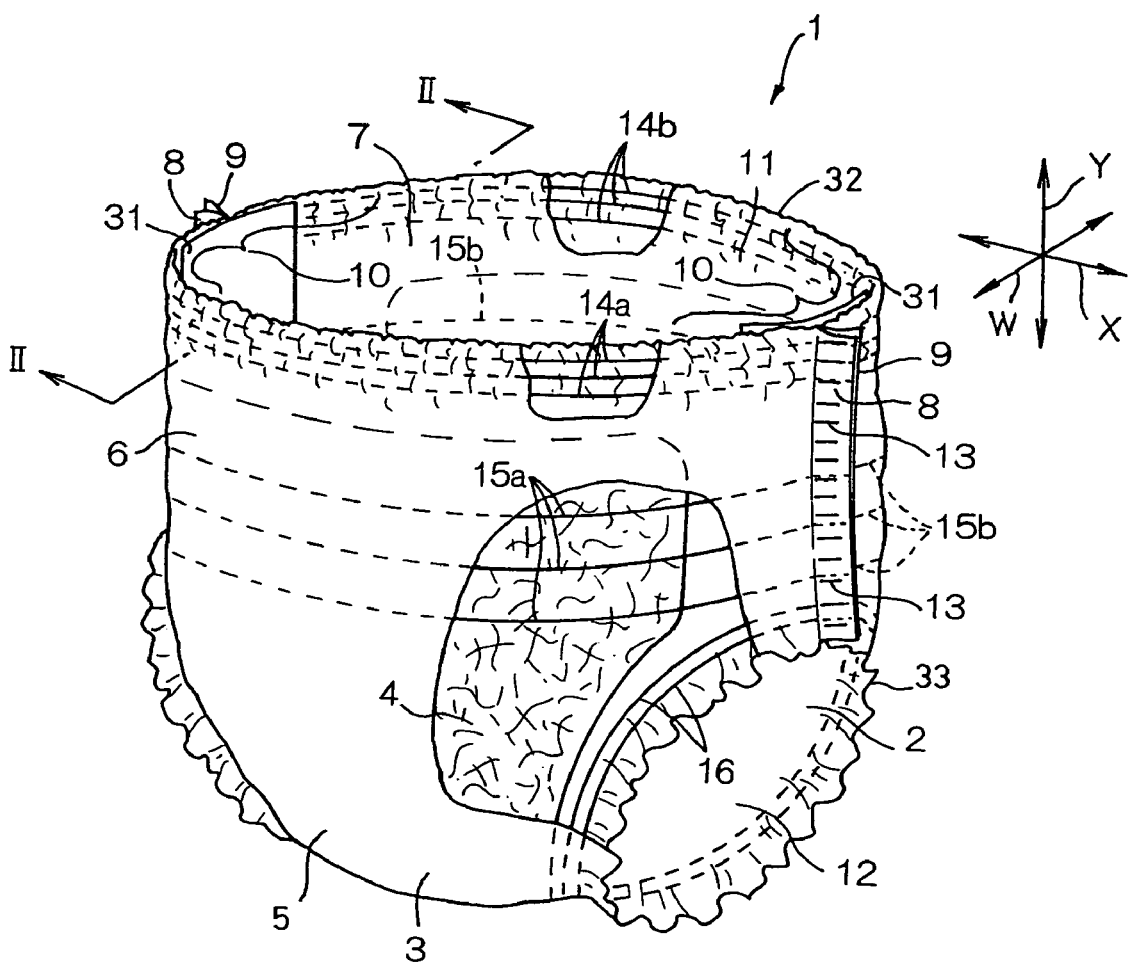
FIG. 1 is a partially cutaway perspective view showing a disposable pull-on type diaper.

FIG. 1 is a partially cutaway perspective view showing a pull-on type diaper 1. The diaper 1 comprises a liquid-pervious inside sheet 2 defining a surface to come in contact with skin of a wearer (not shown), a liquid-impervious outside sheet 3 defining a surface to come in contact with clothes of the wearer and a bodily fluid absorbent core 4 sandwiched between these two sheets 2, 3. The diaper 1 is configured to have a front waist region 6 and a rear waist region 7 which are opposed to each other in a back-and-forth direction W and a crotch region 5. The inside sheet 2 and the outside sheet 3 both extending outward beyond a peripheral edge of the core 4 are overlapped and bonded together by means of hot melt adhesive (not shown) at respective margins defined outside the peripheral edge of the core 4. Specifically, the front waist region 6 has a pair of side edges 8 opposed to each other in a transverse direction X and extending in a vertical direction Y while the rear waist region 7, in a similar fashion, has a pair of side edges 9. Along these side edges 8, 9, the front and rear waist regions 6, 7 are overlapped and bonded together at a plurality of sealing spots 13 arranged intermittently in the vertical direction Y of the diaper 1. Thereupon, the front and rear waist regions 6, 7 cooperate with each other to form a pair of lateral waist zones 10 opposed to each other in the transverse direction X and a waist-opening 11, on one hand, and cooperate with the crotch region 5 to form a pair of leg-openings 12, on the other hand. The front and rear waist regions 6, 7 are provided in the vicinity of a peripheral edge 32 of the waist-opening 11 with a plurality of string-like first waist-surrounding elastic members 14a, 14b sandwiched between the inside sheet 2 and the outside sheet 3 so as to extend in a waist-surrounding direction. Between the peripheral edge 32 of the waist-opening 11 and peripheral edges 33 of the respective leg-openings 12, a plurality of string-like second waist-surrounding elastic members 15a, 15b sandwiched between the outside sheet 3 and the core 4 except for the lateral waist zones 10 in which these second waist-surrounding elastic members 15a, 15b are sandwiched between the outside sheet 3 and the inside sheet 2 so as to extend in the waist-surrounding direction. Each of these first and second waist-surrounding elastic members 14a, 14b, 15a, 15b and leg-surrounding elastic members 16 is bonded in a stretched state to the inside sheet 2 and/or the outside sheet 3. In the diaper 1, inner surfaces of the respective lateral waist zones 10 to come in contact with the wearer's skin is provided with cover sheets 31. Each of the cover sheets 31 extends in the waist-surrounding direction so as to cross the right and left borderlines between the front and rear waist regions 6, 7 and are bonded to the inside sheet 2 in the front and rear waist regions 6, 7.

Figure 2:
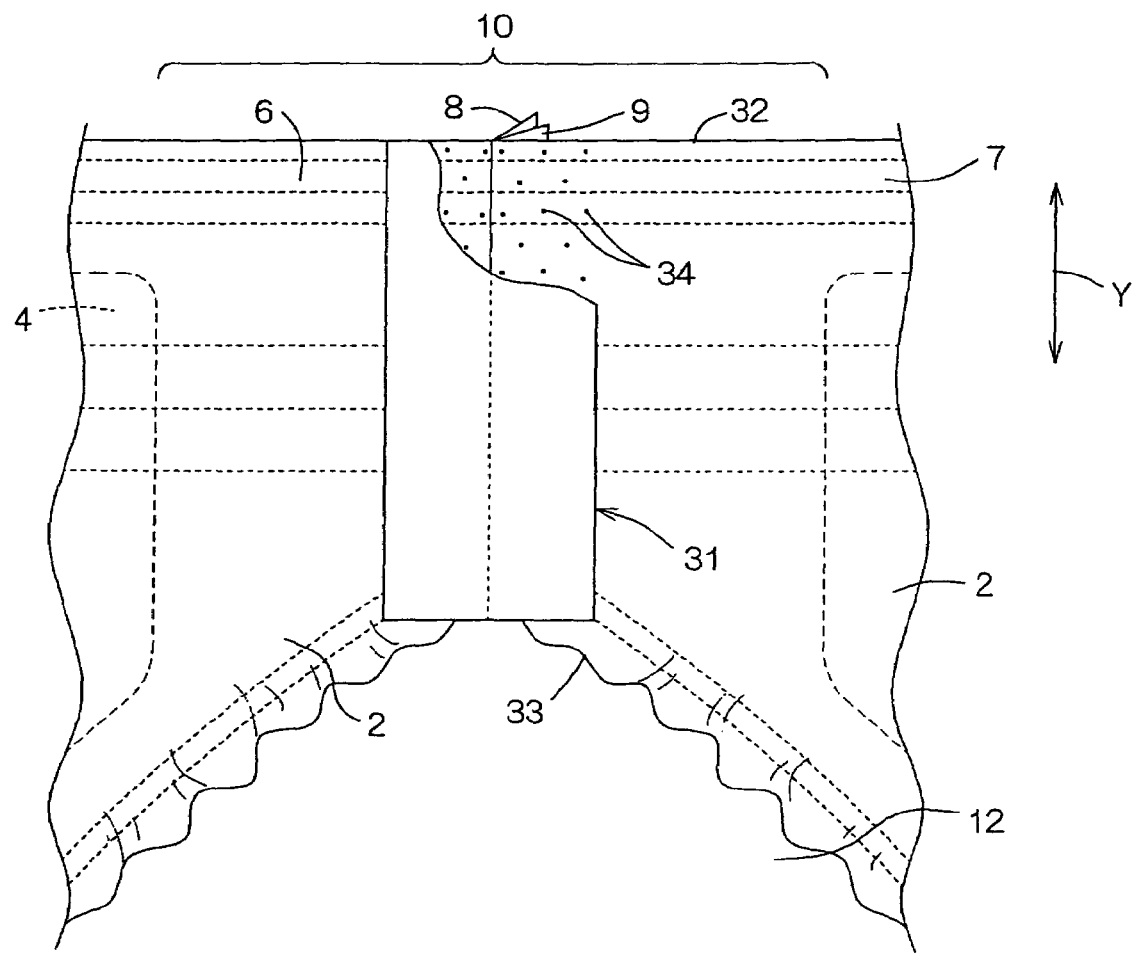
FIG. 2 is a sectional view taken along the line II-II in FIG. 1.

FIG. 2 is a partially cutaway sectional view taken along the line II-II in FIG. 1, showing the cover sheet 31. In the lateral waist zone 10, the cover sheet 31 extends in the vertical direction Y substantially to the peripheral edge 32 of the waist-opening 11 and to the peripheral edge 33 of the associated leg-opening 12 and bonded to the inside sheet 2 in the front and rear waist regions 6, 7 at a plurality of bonding spots 34 illustrated in FIG. 2 in a dot pattern. For possibility that the front and rear waist regions 6, 7 might be disconnected from each other at the sealing spots 13 during use of the diaper 1, these waist regions 6, 7 are firmly bonded to each other. Such sealing spots 13 are the spots of the inside sheet 2 and the outside sheet 3 intrinsically feeling soft and agreeable but converted to the hard blocky structures of hard and rough touch after molten and then solidified. Therefore, if the diaper 1 is not provided with the cover sheets 31, the innermost edge of the sealing spots 13 may be partially exposed on the inner surface of the diaper 1 and uncomfortably irritate the wearer's skin as the diaper 1 is put on the wearer's body with the front and rear waist regions 6, 7 tightened in the waist-surrounding direction. In contrast with such case, the diaper 1 according to the present invention is provided with the cover sheets 31 adapted to cover the innermost edges of the sealing spots 13 which otherwise would be partially exposed on the inner surface of the diaper 1 so that the wearer's skin may be effectively protected from uncomfortable irritation due to the presence of the sealing spots 13. In this way, the cover sheets 31 provided on the inner surface of the diaper 1 effectively solve the problem that the sealing spots 13 at which the front and rear waist regions 6, 7 are connected with each other might come in direct contact with and irritate the wearer's skin from the inside of the diaper 1 put on the wearer's body.

In the diaper 1 according to the present invention, a stock material for the respective components may be selected as will be described hereunder. The inside sheet 2 should be liquid-pervious and may be formed using a thermoplastic sheet material such as a nonwoven fabric made of thermoplastic synthetic fibers having a basis weight in a range of 10 to 50 g/m$^2$ or a perforated film made of a thermoplastic synthetic resin having a thickness in a range of 10 to 30 μm. The outside sheet 3 should be liquid-impervious and may be formed using a nonwoven fabric made of thermoplastic synthetic fibers having a basis weight in a range of 100 to 300 g/m$^2$, a film made of a thermoplastic synthetic resin having a thickness in a range of 10 to 50 μm, a composite sheet composed of the above-mentioned film and nonwoven fabric having an appropriate basis weight laminated on the outer surface of the film so as to provide the outer surface of the film with cloth-like touch, or the like. The core 4 may be exploited in the form of fluff pulp or mixture of fluff pulp and superabsorbent polymer particles covered with a sheet material exhibiting high liquid-permeability as well as high liquid-diffusivity such as a tissue paper. The respective side edges 8, 9 of the front and rear waist regions 6, 7 maybe overlapped with each other and subjected to embossing treatment under heating or to treatment by an ultrasonic sealing machine to form the sealing spots 13 at which the inside sheet 2 is bonded to the inside sheet 2 while the inside sheet 2 is bonded to the outside sheet 3. The cover sheet 31 should present a soft touch and may be formed using a nonwoven fabric having a basis weight in a range of 10 to 50 g/m$^2$ made of thermoplastic synthetic fibers having a fineness in a range of 0.1 to 5 dtx, more preferably, a nonwoven fabric having a basis weight in a range of 10 to 50 g/m$^2$ made of crimped thermoplastic synthetic fibers, a film made of thermoplastic synthetic resin and having a thickness in a range of 10 to 30 μm, more preferably, a film having fine irregularities and air-permeable perforations effective to prevent the film from coming in close contact with the wearer's skin, or the like. The cover sheet 31 may be bonded to the inside sheet 2 at the bonding spots 34 by use of a hot melt adhesive or a sealing technique comprising a step of melting the cover sheet 31 and/or the inside sheet 2 and a step of curing them to integrate them. However, it is a mandatory requirement for the present invention that the wearer's skin should be protected by the cover sheets 31 from irritation due to the sealing spots 13 and at the same time the wearer's skin should be protected from irritation due to the bonding spots 34 of the cover sheets 31. To meet such requirement, if the bonding spots 34 are arranged in dot pattern as illustrated, each of the dots 34 preferably has a diameter less than 2 mm and each pair of the adjacent dots 34 are spaced from each other preferably by 5 mm or more. The distribution of the bonding spots 34 in the dot pattern may be replaced by the distribution in a stripe pattern. In the case of the stripe pattern, each of the stripes 34 preferably has a width narrower than 1 mm and each pair of the adjacent stripes 34 are spaced from each other preferably by 10 mm or more. A plurality of these stripes 34 may extend in parallel one to another in the vertical direction Y or in the waist-surrounding direction. Compared to the stripes 34 extending in the waist-surrounding direction, the stripes 34 extending in the vertical direction Y is advantageous from the viewpoint that the stripes 34 extending in the vertical direction Y are less likely to interfere with expansion and contraction of the front and rear waist regions in the waist-surrounding direction. Instead of forming the bonding spots 34 using adhesive or sealing technique, the cover sheets 31 may be bonded to the inside sheet 2 also by means of a hook member cooperating with a loop member to form a mechanical fastener particularly when the inside sheet 2 is formed from a nonwoven fabric. In this case, the inside sheet 2 functions as the loop member. When both the cover sheets 31 and the inside sheet 2 are formed from a nonwoven fabric, it is also possible to bond the cover sheets 31 to the inside sheet 2 by interlacing the component fibers of both sides together. Like in the needle punching process used for making felt, it is possible to form the bonding spots 34 by guiding the needle so as to pierce the cover sheet 31 and the inside sheet 2 and thereby interlacing the component fibers of these cover sheet 31 and inside sheet 2. The bonding spots 34 formed in this manner are less likely to deteriorate flexibility of the lateral waist zones 10 than the bonding spots 34 formed using adhesive or sealing technique.

The present invention which has been described above with respect to the disposable pull-on type diaper 1 as one specific embodiment may be exploited in the form of disposable pants, disposable training pants, or disposable pull-on type wearing article used as a chassis for a urine absorbent pad or sanitary napkin. While the side edges 8, 8 of the front waist region 6 and the side edges 9, 9 of the rear waist region 7 are illustrated to be overlapped with each other and sealed together, it is also possible to place the side edges 8, 8 upon the side edges 9, 9 and then to seal them together so that the inner surface of the side edges 8 may be opposed to the outer surface of the side edges 9 or vice versa. While the lateral waist zones 10 are illustrated to be formed by overlapping the inside sheet 2 and the outside sheet 3 each other, it is possible to form the lateral waist zones 10 by dimensioning the outside sheet 3 to be longer than the inside sheet 2 in the waist-surrounding direction so that the portions of the outside sheet 3 extending beyond the side edges of the inside sheet 2 may define the respective lateral waist zones 10. It is also possible to form the lateral waist zones 10 by attaching separately provided sheet strips to the inside sheet 2 and/or the outside sheet 3 so as to extend in the waist-surrounding direction. The cover sheets 31 may be bonded to the inner surface of the outside sheet 3 or the inner surface of the separately provided sheet strips forming the lateral waist zones 10 in the manner as has been described above.

The present invention may be used to improve the pull-on type wearing article having the front and rear waist regions integrated with each other at the sealing spots arranged intermittently along the side edges of these two waist regions so that the wearer's skin is reliably protected from stimulation due to the presence of the sealing spots.

The entire discloses of Japanese Patent Application No. 2005-77731 filed on Mar. 17, 2005 including specification, drawings and abstract are herein incorporated by reference in its entirety.

What is claimed is:

1. A disposable pull-on type wearing article, comprising:
   a main diaper body comprising:
   a front waist region;
   a rear waist region;
   a crotch region;
   said front and rear waist regions respectively having side edges opposed to each other in a transverse direction of the article;
   said front and rear waist regions being overlapped with each other along said side edges and integrated together at a plurality of sealing spots to define a waist-opening, a pair of leg-openings, and lateral waist zones including respective border lines opposed to each other in said transverse direction; and
   a plurality of cover sheets made separately from said main diaper body, each of said cover sheets being bonded to said front and rear waist regions on an inner surface adapted to contact with wearer's skin in respective said lateral waist zones, wherein each of said cover sheets covers one of the border lines between said front and rear waist regions and, in addition to the integration of said waist regions at said sealing spot, holds the waist regions together against separation.

2. The wearing article as claimed in claim 1, wherein said cover sheets extend in said lateral waist zones between said waist-opening and respective said leg-openings.

3. The wearing article as claimed in claim 1, wherein said cover sheets are bonded to said front and rear waist regions by at least one of adhesion, sealing and interlacing of component fibers contained in said front and rear waist regions and said cover sheets.

4. The wearing article as claimed in claim 1, wherein each of said cover sheets has opposite first and second surfaces, the first surface being adapted to contact the wearer's skin in use, and the second surface being adapted to face away from the wearer's skin in use and being directly attached to both the front and rear waist regions on opposite sides of the respective border line.

5. The wearing article as claimed in claim 4, wherein the second surface of each of said cover sheets is directly bonded to both the front and rear waist regions at a plurality of bonding spots, the bonding spots being arranged in a dot pattern.

6. The wearing article as claimed in claim 5, wherein each dot of the dot pattern has a diameter less than 2 mm, and adjacent dots of the dot pattern are spaced from each other at least by 5 mm.

7. The wearing article as claimed in claim 4, wherein the second surface of each of said cover sheets is directly bonded to both the front and rear waist regions at a plurality of bonding spots, the bonding spots being arranged in a stripe pattern extending in the transverse direction.

8. The wearing article as claimed in claim 7, wherein each stripe of the stripe pattern has a width less than 1 mm and adjacent stripes of the stripe pattern are spaced from each other at least by 10 mm.

9. The wearing article as claimed in claim 4, wherein the second surface of each of said cover sheets is directly to both the front and rear waist regions at a plurality of bonding spots, the bonding spots being arranged in a stripe pattern extending in a longitudinal direction between the waist opening and the leg openings and along the border lines.

10. The wearing article as claimed in claim 9, wherein each stripe of the stripe pattern has a width less than 1 mm and adjacent stripes of the stripe pattern are spaced from each other at least by 10 mm.

11. The wearing article as claimed in claim 4, wherein the second surface of said cover sheet comprises hooks engaging with matching loops on the inner surface in both said front and rear waist regions.

12. The wearing article as claimed in claim 4, wherein each of said cover sheets has opposite edges, and the second surface of said cover sheet is directly bonded to the inner surface of the front waist region along one of the edges and is directly bonded to the inner surface of said rear waist region along the other edge.

13. The wearing article as claimed in claim 12, wherein each of said edges of the cover sheet is spaced in the transverse direction from the respective border line.

14. The wearing article as claimed in claim 13, wherein the second surface of each of said cover sheets is directly bonded to both the front and rear waist regions at a plurality of bonding spots, said spots being arranged on both said sides of the respective border line and between the edges of the cover sheet.

15. The wearing article as claimed in claim 14, wherein the bonding spots are arranged in a dot pattern.

16. The wearing article as claimed in claim 14, wherein the bonding spots are arranged in a stripe pattern extending in the transverse direction.

17. The wearing article as claimed in claim 14, wherein the bonding spots are arranged in a stripe pattern extending in a longitudinal direction between the waist opening and the leg openings and along the border lines.

18. The wearing article as claimed in claim 14, wherein, at the bonding spots, component fibers of said cover sheet and component fibers on the inner surface of said waist regions are interlaced.

19. The wearing article as claimed in claim 1, wherein each of said cover sheets is a nonwoven fabric having a basis weight in a range of 10 to 50 g/m and having a fineness in a range of 0.5 to 5 dtx.

\* \* \* \* \*